United States Patent [19]

Möhring et al.

[11] 4,300,003
[45] Nov. 10, 1981

[54] PROCESS FOR THE PREPARATION OF LOW MOLECULAR POLYHYDROXYL COMPOUNDS

[75] Inventors: Edgar Möhring, Bergisch-Gladbach; Hanns P. Müller; Kuno Wagner, both of Leverkusen, all of Fed. Rep. of Germany

[73] Assignee: Bayer Aktiengesellschaft, Leverkusen, Fed. Rep. of Germany

[21] Appl. No.: 55,655

[22] Filed: Jul. 6, 1979

[30] Foreign Application Priority Data

Jul. 19, 1978 [DE] Fed. Rep. of Germany ....... 2831656

[51] Int. Cl.³ .............................................. C07C 31/18
[52] U.S. Cl. .................................. 568/863; 568/672; 521/158
[58] Field of Search ........................................ 568/863

[56] References Cited

U.S. PATENT DOCUMENTS

| | | | |
|---|---|---|---|
| 2,121,981 | 12/1934 | Prudhomme | 204/31 |
| 2,224,910 | 12/1940 | Hanford et al. | 226/730 |
| 2,269,935 | 2/1940 | Hanford et al. | 260/594 |
| 2,271,083 | 1/1942 | Leonard | 260/635 |
| 2,272,378 | 2/1942 | Lorand | 260/594 |
| 2,276,192 | 3/1942 | Hanford et al. | 260/635 |
| 2,760,983 | 8/1956 | Machean et al. | 260/594 |
| 2,775,621 | 12/1956 | Machean et al. | 260/635 |

FOREIGN PATENT DOCUMENTS

| | | |
|---|---|---|
| 705274 | 4/1941 | Fed. Rep. of Germany . |
| 725842 | 10/1942 | Fed. Rep. of Germany . |
| 822385 | 7/1949 | Fed. Rep. of Germany . |
| 884791 | 7/1949 | Fed. Rep. of Germany . |
| 830951 | 2/1952 | Fed. Rep. of Germany . |
| 888096 | 8/1953 | Fed. Rep. of Germany . |
| 1044157 | 12/1955 | Fed. Rep. of Germany . |
| 2732077 | 2/1975 | Fed. Rep. of Germany . |
| 2639084 | 8/1977 | Fed. Rep. of Germany . |
| 2714084 | 10/1978 | Fed. Rep. of Germany . |
| 2714104 | 10/1978 | Fed. Rep. of Germany . |
| 2721093 | 11/1978 | Fed. Rep. of Germany . |
| 513708 | 10/1939 | United Kingdom . |
| 745557 | 2/1956 | United Kingdom ................ 568/863 |
| 1542980 | 8/1977 | United Kingdom . |

OTHER PUBLICATIONS

Butlerow and Loew (Ann. 120, 295 (1861) and J. Prakt. Chem., 33 321 (1886).
R. D. Partridge and A. H. Weiss, Carbohydrate Research 24, 29–44 (1972).
Pfiel, Chem. Berichte 84, 229 (1957).
Pfiel & Scheoth, Chem. Berichte, 85, 303 (1952).
R. D. Partridge, A. H. Weiss & D. Todd, Carbohydrate Research, 24 (1972), 42.
L. Orthner & E. Gerisch, (Biochem. Zeirung, 259, 30 (1933).

*Primary Examiner*—Joseph E. Evans
*Attorney, Agent, or Firm*—Gene Harsh; Joseph C. Gil; Lyndanne M. Whalen

[57] ABSTRACT

Formose solutions are hydrogenated in a batchwise alkaline two-stage catalytic process to produce low molecular weight polyhydric alcohols.

8 Claims, No Drawings

PROCESS FOR THE PREPARATION OF LOW MOLECULAR POLYHYDROXYL COMPOUNDS

BACKGROUND OF THE INVENTION

This invention relates to an improved process for the preparation of low molecular polyalcohols. This process comprises an alkaline two-stage catalytic hydrogenation of a mixture of various low molecular weight hydroxyaldehydes, hydroxyketones and polyhydric alcohols which is obtained from the autocondensation of formaldehyde (such a mixture will hereinafter be referred to as "formose"). The invention also relates to the use of these polyalcohols for the production of polyurethanes.

Since the work of Butlerow and Loew (Ann. 120, 295 (1861) and J. prakt, Chem. 33, 321 (1886)) in the previous century it has been known that hydroxyaldehydes, hydroxyketones and polyhydric alcohols are formed when the autocondensation of formaldehyde hydrate (formose synthesis) is carried out under the influence of basic compounds such as calcium or lead hydroxide. Studies on the synthesis of formose have repeatedly been carried out since then. References in this connection include Pfeil, Chem. Berichte 84, 229 (1951), Pfeil and Schroth, Chemische Berichte 85, 303 (1952), R. D. Partridge and A. H. Weiss, Carbohydrate Research 24, 29–44 (1972), Formoses from Glyceraldehyde and Dihydroxyacetone according to Emil Fischer, German Pat. Nos. 822,385, 830,951 and 884,791, U.S. Pat. Nos. 2,121,981, 2,224,910, 2,269,935 and 2,272,378 and British Pat. No. 513,708. All these processes known in the art have certain disadvantages (poor volume/time yields, discolored by-products), but new processes have recently been developed, by which substantially colorless formoses free from undesirable by-products can be produced in high yields with the aid of conventional catalysts.

One of these new processes consists of carrying out the condensation of formaldehyde hydrate in the presence of catalysts consisting of soluble or insoluble lead-(II) salts or of lead (II) ions bound to high molecular weight carriers and in the presence of formose as a cocatalyst.

The reaction temperature employed is generally in the range of from 70° to 110° C., and preferably from 80° to 100° C. The pH of the reaction solution is adjusted by the controlled addition of an inorganic and/or organic base to a value of from 6.0 to 8.0, and preferably from 6.5 to 7.0 up to a conversion of from 10 to 60%, and preferably from 30 to 50%. Thereafter, the pH is adjusted to a value of from 4.0 to 6.0, and preferably from 5.0 to 6.0. It was surprisingly found that this special pH control and subsequent cooling at different residual formaldehyde contents (from 0 to 10% by weight, and preferably from 0.5 to 6.0%, by weight) enables the proportion of products obtained to be varied in a reproducible manner.

When the autocondensation of formaldehyde hydrate has been stopped by cooling and/or by deactivation of the lead-catalyst by means of acids, the catalyst, and optionally also the water contained in the products is removed. Further details of these processes may be found in German Offenlegungsschriften Nos. 2,639,084 and 2,732,077.

Another possibility of obtaining highly concentrated, colorless formoses in high volume/time yields consists of a process described in German Offenlegungsschrift No. 2,714,084. In this process, aqueous formalin solutions and/or paraformaldehyde dispersions are condensed in the presence of a soluble or insoluble metal catalyst and a cocatalyst which has been obtained by the partial oxidation of a dihydric or higher hydric alcohol having a molecular weight of from 62 to 242 and containing at least two adjacent hydroxyl groups or a mixture of such alcohols. In this process, the pH of the reaction solution is controlled by the controlled addition of a base so that it is maintained at from 6.0 to 9.0 up to a conversion of from 5 to 40% and is then adjusted to from 4.5 to 8.0 until the condensation reaction is stopped. In the second stage, the pH is lower by from 1.0 to 2.0 units than in the first stage of the reaction. The reaction is stopped by the deactivation of the catalyst when the formaldehyde content has fallen to a level of from 0 to 10% by weight, and the catalyst is subsequently removed.

High quality formoses can also be obtained by the condensation of formaldehyde in the presence of a metal catalyst and more than 10% by weight, based on the formaldehyde, or one or more divalent or higher valent low molecular weight alcohols and/or higher molecular polyhydroxyl compounds (see German Offenlegungsschrift No. 2,714,104).

It is particularly economical to produce formoses directly from formaldehyde-containing synthesis gases according to German Offenlegungsschrift No. 2,721,093, i.e., without going through the stages of preparation of aqueous formalin solutions or paraformaldehydes. For this purpose, synthesis gases such as are obtained from the large scale production of formaldehyde are introduced continuously or intermittently, at a temperature of from 10° to 150° C., into an absorption liquid which is at a pH of from 3 to 10. This absorption liquid consists of water, monohydric or higher hydric low molecular weight alcohols and/or higher molecular polyhydroxyl compounds and/or compounds capable of enediol formation as cocatalysts and/or soluble or insoluble metal compounds optionally bound to high molecular weight carriers as catalysts. The formaldehyde is directly condensed in situ in the absorption liquid (optionally also in a following reaction tube or cascade of stirrer vessels). Autocondensation of formaldehyde is stopped by cooling and/or deactivation of the catalyst with acids when the residual formaldehyde content in the reaction mixture is from 0 to 10% by weight, and the catalyst is finally removed.

For various applications, the mixtures of hydroxyaldehyde, hydroxyketones and polyalcohols obtained by the process described above or known art processes must be converted into mixtures of polyalcohols by reduction of the carbonyl groups. (Such polyol mixtures obtained by the reduction of formoses will hereinafter be referred to as "formitols".) The reduction of formose may, for example, be carried out in aqueous solution at room temperature using sodium borohydride (see R. D. Partridge, A. H. Weiss and D. Todd, Carbohydrate Research 24 (1972), 42). On the other hand, it may be carried out using an electrochemical method.

Many processes for the catalytic hydrogenation of sugars as well as of formoses are known. Very different quantities and types of catalysts are used, depending on the process. Thus L. Orthner and E. Gerisch (Biochem. Zeitung 259, 30 (1933)) describe a process for the catalytic hydrogenation of formose in which a 4% aqueous formose solution is hydrogenated using 170%, by weight of Raney nickel, based on the quantity of formose, in a reaction lasting for from 7 to 8 hours at a temperature of 130° C. and a hydrogen pressure of 120 bar. Such a process is, of course, economically unsatisfactory.

In U.S. Pat. No. 2,269,935, there has been disclosed a process in which a solution containing approximately 40% by weight of formose is hydrogenated at an acidic pH using 20% by weight of a nickel catalyst at a hydrogen pressure of from 600 to 620 bar and at a temperature of 120° C. The disadvantages of this variation of the process are not only the high operating pressure but also the low pH value necessary, which results in green colored products due to nickel ions.

In U.S. Pat. No. 2,224,910, there is disclosed a process for the hydrogenation of formose in which a 40% formose solution is hydrogenated using 30% by weight of Raney nickel, based on formose, at a hydrogen pressure of from 140 to 210 bar and at pH of 7 for 4 hours. This process again is unsatisfactory due to the large quantity of catalyst used and the long reaction time required.

Other hydrogenation processes have been described in German Pat. Nos. 705,274, 725,842, 830,951, 888,096 and 1,044,157 and in U.S. Pat. Nos. 2,271,083, 2,272,378, 2,276,192, 2,760,983 and 2,775,621. All these processes have one or more of the following disadvantages: large and expensive apparatus, difficulty of handling due to high hydrogen pressures, high catalyst consumption based on the quantity of hydrogenated product (from 10 to 200% by weight) and colored products due to long hydrogenation times (from 1 to 10 hours). Common also to all the known hydrogenation processes is the use of metal catalysts and in some cases noble metal catalysts. It is particularly common to use Raney nickel. As is known in the case, Raney nickel only develops its full activity in the alkaline pH range. Since formose tends to undergo caramelization in an alkaline medium and heavily discolored products are formed, the processes known in the art are generally not carried out at an alkaline pH but in a slightly acidic to neutral pH range.

According to an earlier proposal by the present Applicants (U.S. application Ser. No. 965,645, filed Dec. 1, 1978), formose solutions (optionally as mixtures with other natural and/or synthetic sugars) can be rapidly hydrogenated in a highly alkaline medium with a low consumption of catalyst at a hydrogen pressure of from 100 to 200 bar and at a temperature of from 50° to 250° C. to form colorless solutions of polyol mixtures. In the process according to U.S. application Ser. No. 965,645, a formose solution at a concentration of more than 20% is pumped batchwise into a reactor which is at a temperature of from about 100° to 200° C. at a rate such that the concentration of the groups which are to be reduced does not rise above 2% by weight. Hydrogenation is carried out at a pH value of from 7.5 to 12.5 with a catalyst consumption of from $10^{-4}$ to $5\times 10^{-2}\%$ by weight (based on formose) and at a hydrogen pressure of from 50 to 300 bar. The catalysts used are, in particular, metals having an atomic number of from 23 to 29 (and especially Raney nickel).

When the formitol solutions obtained by the known hydrogenation processes are concentrated, for example, by thin layer distillation in a vacuum, troublesome yellow discolorations of hitherto unknown cause generally occur, regardless of the particular process used for the preparation of the formose solution and the conditions of hydrogenation.

DESCRIPTION OF THE INVENTION

It has now surprisingly been found that the discoloration which normally occurs during concentration of the formitol solutions can be completely prevented if a special two-stage process is used for hydrogenation. In the first stage, formose is hydrogenated in an alkaline medium, preferably in the presence of a Raney metal catalyst. The pH of the solution is then adjusted to a value of from 1 to 6. The solution is subsequently made alkaline again and rehydrogenated in a second stage in an alkaline medium.

The present invention thus relates to a process for the preparation of low molecular weight, polyhydric alcohols by the hydrogenation of formose solutions in the presence of metal catalysts, which comprises (A) introducing a formose solution, the pH of which solution has been adjusted to a value in the range of from 7.5 to 12.5 (preferably from 8.5 to 11.5), at a concentration of at least 20% by weight, and preferably more than 35%, (most preferably more than 45%), batchwise into a first reactor, (which is preferably maintained at a temperature of from 100° to 200° C., and most preferably at from 140° to 190° C.), the rate of introduction being such that the concentration of reducible groups (determined as carbonyl groups) in the product mixture inside the reactor does not exceed 2% by weight (and preferably does not exceed 1% by weight and most preferably does not exceed 0.5% by weight);

(B) hydrogenating the solution batchwise in the presence of a total quantity of catalyst of from $10^{-4}$ to $5\times 10^{-2}\%$ by weight, based on the total quantity of starting material to be reduced, the catalyst content remaining constant inside the reactor;

(C) removing the reaction product batchwise from the reactor when the concentration of reducible groups (determined as carbonyl groups) has fallen below 1.5% by weight, preferably below 0.5% by weight;

(D) adjusting the pH of this prehydrogenation reaction product to a value of from 1 to 6, preferably from 1 to 4.5;

(E) introducing the reaction product thus obtained batchwise into a second reactor which is preferably maintained at a temperature of from 50° to 250° C., most preferably from 100° to 200° C., the pH of said product having been readjusted to a value of from 7.5 to 12.5, preferably from 8.5 to 11.5 immediately before its being pumped into the second reactor;

(F) hydrogenating the product batchwise in the presence of a total quantity of catalyst of from $10^{-4}$ to $5\times 10^{-2}\%$ by weight, based on the total quantity of product which has been prehydrogenated in the first reactor, the catalyst content remaining constant in the second reactor; and (G) withdrawing the reaction product batchwise from the second reactor after a dwell time of from 5 minutes to 4 hours, and preferably from 10 minutes to 60 minutes.

The process according to the present invention is particularly advantageously carried out as follows. The quantity of catalyst (preferably Raney nickel) required to hydrogenate the whole batch is introduced in water into a pressure reactor. The reactor is then filled with gaseous hydrogen to an operating pressure of from 50 to 300 bar and heated to the hydrogenation temperature of from 80° to 220° C. From 3 to 30 times the quantity by weight of formose solution (preferably from 5 to 20 times the quantity), based on the catalyst, is then slowly pumped into the first reactor (i.e. about 1/6 of the volume of the reactor is filled in from 3 minutes to 2 hours, preferably from 5 to 30 minutes). Hydrogenation is then carried out for a length of time amounting to from half to 4 times the time required for pumping in the formose solution. The quantity of reaction mixture corresponding to the quantity of formose solution added is then forced out through a frit having a steel jacket while the catalyst remains in the reactor. A fresh batch is then pumped into the reactor and treated in the same way as the first batch. All subsequent batches are treated in the same manner. Each batch leaving the first reactor is then, preferably immediately thereafter, maintained at a pH value of from 1 to 6 and a temperature of from 10° to 100° C. for from 10 minutes to 2 hours, preferably from 15 minutes to one hour, and is thereafter adjusted to a pH value of from 7.5 to 12.5. The solution is subsequently introduced into a second reactor.

This second reactor also preferably contains the total quantity of catalyst in water required to hydrogenate the total quantity of product which has been prehydrogenated in the first reactor. The reactor is filled with hydrogen gas to an operating pressure of from 50 to 300 bar and then heated to the hydrogenation temperature of from 50° to 250° C. The prehydrogenated formose solution is preferably introduced by pumping from 3 to 30 times (most preferably from 5 to 20 times) the quantity of formose solution, based on the quantity of catalyst, slowly into the reactor (i.e. at a rate corresponding to a filling of approximately 1/6 of the volume of the reactor in from 3 minutes to 2 hours, preferably from 5 to 30 minutes). Hydrogenation is then carried out for a period of time amounting to from ½ to 5 times the length of time taken to pump in the prehydrogenated solution. The same quantity of reaction product is then forced out through a steel jacketed frit while the catalyst is left in the reactor. The next batch from the first reactor is then pumped into the second reactor after it has been acidified and again made alkaline, and this second batch is then treated in the same way as the first. All subsequent batches are treated in the same manner.

This two-stage batchwise pumping hydrogenation according to the present invention enables an extremely long catalyst life to be obtained both for the first stage and for the second stage and hence very low catalyst consumption, based on the total quantity of formose reduced.

The process of the instant invention possesses all the advantages of pump hydrogenation of formose described in U.S. Ser. No. 965,645 compared with the known art processes, such as (1) great economy of the process due to low catalyst consumption and short hydrogenation times; (2) low commercial expense due to relatively low hydrogen pressures; (3) extensive decomposition of the starting materials into low molecular $C_2$ to $C_5$ alcohols, whereby the viscosity of the polyhydroxyl compound is lowered, their processibility improved, and at the same time their compatibility with other substances increased, and especially their compatibility with the starting components used for the production of synthetic materials by the polyisocyanate polyaddition process (in particular higher molecular weight polyhydroxyl compounds and blowing agents); (4) possibility of adding other compounds such as alkanals, monohydric or polyhydric alcohols, ketones, aldehydes or higher molecular weight polyols in quantities of up to 50% by weight (based on the total quantity of products to be reduced) of the formose to be hydrogenated, if desired because they improve, in particular, the compatibility of the reaction products with the blowing agents used in the polyisocyanate polyaddition process; (5) the possibility of also hydrogenating other natural and/or synthetic sugars apart from formose by the process according to the invention.

The process according to the present invention has the additional important advantage of producing colorless polyol mixture solutions which can be concentrated by evaporation at a temperature of up to 180° C. without any discoloration. This is particularly advantageous since for numerous applications the polyhydroxyl compounds obtainable by the hydrogenation of formose can only be used after the removal of the water used as solvent. Such removal, however, may render the products useless due to the discoloration produced (e.g. when the product is to be used as polyol component in polyurethane lacquers).

Suitable aldehydes or alkanals which may also be used in the process according to the present invention include, in particular acetaldehyde, propionaldehyde, butyraldehyde, isobutyraldehyde and their methylol derivatives.

Suitable ketones include acetone, methyl ethyl ketone, diethyl ketone, cyclopentanone, cyclohexanone, mesityl oxide, isophorone, acetophenone, benzophenone and their methylol derivatives.

The most important solvent for use in the process according to the present invention is water although the formoses may also be dissolved in any monohydric or polyhydric alcohols. The following are examples of suitable alcohols: methanol, ethanol, propanol, butanol, isopropanol, isobutanol cyclopentanol, cyclohexanol, 2-ethoxyethanol, 2-propoxyethanol, 2-isopropoxyethanol, 2-butoxyethanol, 2-(2-methoxyethoxy)-ethanol, 2-(2-ethoxyethoxy)-ethanol, 1,2-bis-(2-hydroxyethoxy)-ethane, ethylene glycol, diethylene glycol, triethylene glycol, tetraethylene glycol, 1,2-propanediol, isopropylene glycol, 1,3-propanediol, 1,2-butanediol, 1,3-butanediol, 2-methoxy-1-butanol, 2,3-butanediol, 1,5-pentanediol, 2,2-dimethyl-1,3-propanediol, 1,6-hexanediol, 2,5-hexanediol, 2-methyl-2,4-pentanediol, 3-methyl-1,5-pentanediol, 3-methyl-2,4-pentanediol, 2,3-dimethyl-2,3-butanediol, 2-methyl-2-propyl-1,3-propanediol, 2,2-diethyl-1,3-propanediol, 2-ethyl-1,3-hexanediol, 2,5-dimethyl-2,5-hexanediol, 2,2,4-trimethyl-1,3-pentanediol, 1,3-diethoxy-2-propanol, 2-hydroxymethyl-2-methyl-1,3-propanediol, 1,2,6-hexanetriol, 2-ethyl-2-hydroxymethyl-1,3-propanediol, 2,2-bis-hydroxymethyl-1,3-propanediol, erythritol, quinitol, mannitol, sorbitol and methyl glycoside and ethoxylation and propoxylation products of these alcohols having a molecular weight of up to about 400 and, of course, also mixtures of these alcohols. Ethylene glycol, glycerol and 1,4-butanediol are particularly preferred.

According to the present invention, polyhydroxyl compounds having a molecular weight of from 400 to 10,000, preferably from 500 to 6000, may also be included in the hydrogenation process, optionally as mixtures with the above-mentioned alcohols. Thee polyhydroxyl compounds should preferably also be liquid at room temperature or soluble in the formose solution. Examples include polyesters, polyethers, polythioethers, polyacetals, polycarbonates and polyester amides having at least two, generally from 2 to 8, preferably from 2 to 4 hydroxyl groups, such as the compounds of this type which are known for the production of both homogeneous and cellular polyurethanes.

The hydrogenation process according to the present invention is applicable to substantially any formose, but the formoses may also be used as mixtures with up to 80% by weight (based on the total quantity of compounds to be hydrogenated) of other artificial or natural sugars (such as glucose, maltose, fructose, saccharose, lactose, and the like). It is particularly advantageous that formose is known as an excellent solvent or solubilizing agent for such sugars.

The artificial invert sugars which may be included in the process according to the invention may be hydrolysates of any di- and/or polysaccharides, e.g. of cane sugar, mixtures of cane sugar and invert sugars, hydrolysates of trehalose, maltose or isomaltose, hydrolysates of corn starch and potato starch and of pectins (amylose and aminopectins), cellobiose and lactose, hydrolysates of galactose, and glucose mixtures, raffinose hydrolysates, cellulose hydrolysates, hydrolysates of dextrins, optionally mixed with non-hydrolyzed dextrins, hydrolysates of Schardinger dextrins (cyclic dextrins), hydrolysates of glycogen, hydrolysates of glucose-6-phosphoric acid, hydrolysates of glucose-1-phosphate (Cori esters), fructose-6-phosphate, degraded pectins (polygalacturonic acids), degraded glucosamines, hydrolysates of molasses residues, and the like.

In both stages of the process according to the present invention, the pH of the solution to be hydrogenated may be adjusted either with inorganic or with organic bases. It is preferred to use sodium hydroxide, potassium hydroxide, calcium hydroxide, magnesium hydroxide, barium hydroxide, aluminum hydroxide, triethylamine, N-methylmorpholine or N-methylpiperidine. It is particularly preferred to use the base which has been used for the formose synthesis. Before hydrogenation, this base is converted into the free OH form by treatment of the formose solution with an ion exchange resin which is in the OH form. By this method, the pH of the formose solution is automatically adjusted to the required alkalinity.

For acidification between the first and second stages of the process according to the present invention, it is suitable to use mineral acids such as hydrochloric acid, nitric acid or phosphoric acid or organic acids such as oxalic acid, formic acid or acetic acid, and strongly acid cation exchange resins preferably in the H$^\oplus$ form.

Suitable hydrogenation catalysts for the process according to the present invention include, in particular, metals having an atomic number in the range of from 23 to 29 (in their elementary and/or oxidic form). Suitable catalysts include, for example, those based on nickel or cobalt, using as a catalyst carrier either inorganic materials (such as kieselguhr, silicates, aluminum oxides, alkali metal and alkaline earth silicates, aluminum silicates, montmorillonite, zeolites, spinels, dolomite, kaolin, magnesium silicates, zirconium oxide, iron oxide, zinc oxide, calcium carbonate, silicon carbide, aluminum phosphate, borophosphate, asbestos or active charcoal) or organic materials (such as naturally occurring or synthetic compounds having a high molecular weight, such as silk, polyamides, polystyrenes, cellulose or polyurethanes). The catalyst carrier may be, for example, in the form of spheres, strands, threads, cylinders, polygons or powders. Raney type catalysts such as Raney nickel, W-1-, W-5-, W-6- and W-7-Raney nickel (see H. Adkins, J. Am. Chem. Soc. 69, 3039 (1974)), Raney cobalt catalysts, Raney copper, Raney nickel iron, Raney cobalt nickel and Raney cobalt iron are preferred. Metal catalysts prepared by the reduction of nickel or cobalt salts may also be used, such as Urushibara nickel, nickel or cobalt salts which have been reduced with metal alkyl compounds, alkali metal hydrides, hydrazine, boranates or hydrogen boride, catalyts prepared by reduction of the metal oxides or metal oxide mixtures, or the metal oxides or oxide mixtures themselves.

The preferred catalysts according to the present invention, which are based on metals having an atomic number of from 23 to 29, may contain one of the following elements as accelerators in quantities of up to 10% by weight: Li, Na, Ca, Ba, K, Ag, Be, La, Ce, V, Nb, Ta, Mo, W and up to 1% by weight of the elements Ru, Rh, Pd, Au, Ir, and Pt.

Particularly suitable catalysts are Raney nickel containing 90% by weight of Ni and <1% by weight of Fe, Ca and Na, Raney nickel iron containing from 5 to 30% by weight of Fe and <1% by weight of Ca and Na and Raney cobalt iron containing from 10 to 30% by weight of Fe.

The preferred use of the mixtures of polyhydric, low molecular alcohols prepared according to the present invention is as polyol components in the polyisocyanate polyaddition process.

The present invention thus also relates to a process for the preparation of cellular or non-cellular polyurethanes comprising reacting:

(A) polyisocyanates with
(B) compounds having a molecular weight of from 32 to 400 which have at least two active hydrogen atoms, optionally
(C) compounds having a molecular weight of from 400 to 10,000 which have at least two active hydrogen atoms and optionally
(D) blowing agents, catalysts and other known additives, characterized in that component (B) comprises mixtures of polyhydric alcohols prepared according to the present invention.

As starting components for the production of polyurethanes, aliphatic, cycloaliphatic, araliphatic, aromatic and heterocyclic polyisocyanates such as those described e.g. by W. Siefken in Justus Liebigs Annalen der Chemie, 562, pages 75 to 136, for example, those corresponding to the following general formula:

$$Q(NCO)_n$$

wherein
n represents 2–4, preferably 2, and
Q represents an aliphatic hydrocarbon group having from 2–18, preferably from 6–10 carbon atoms,
a cycloaliphatic hydrocarbon group having from 4–15, preferably from 5–10 carbon atoms,
an aromatic hydrocarbon group having from 6–15, preferably from 6–13 carbon atoms,
or an aliphatic hydrocarbon group having from 8 to 15, preferably from 8–13 carbon atoms.

Examples of suitable isocyanates include: ethylene diisocyanate; 1,4-tetramethylene diisocyanate; 1,6-hexamethylenediisocyanate; 1,12-dodecanediisocyanate; cyclobutane-1,3-diisocyanate; cyclohexane-1,3- and -1,4-diisocyanate and mixtures of these isomers; 1-isocyanato-3,3,5-trimethyl-5-isocyanatomethylcyclohexane (German Auslegeschrift No. 1,202,785, U.S. Pat. No. 3,401,190); 2,4- and 2,6-hexahydrotolylene diisocyanate and mixtures of these isomers; hexahydro-1,3- and/or 1,4-phenylene diisocyanate; perhydro-2,3'- and/or 4,4'-diphenylmethane diisocyanate; 1,3- and 1,4-phenylene-diisocyanate; 2,4- and 2,6-tolylene-diisocyanate and mixtures of these isomers; diphenylmethane-2,4'- and/or -4,4'-diisocyanate; naphthylene-1,5-diisocyanate; triphenylmethane-4,4',4''-triisocyanate; polyphenyl-polymethylene polyisocyanates which may be obtained by aniline/formaldehyde condensation followed by phosgenation and which have been described, e.g. in British Pat. Nos. 874,430 and 848,671; m- and p-isocyanatophenyl-sulphonylisocyanates as described in U.S. Pat. No. 3,454,606; perchlorinated aryl polyisocyanates as described e.g. in German Auslegeschrift No. 1,157,601 (U.S. Pat. No. 3,277,138); polyisocyanates containing carbodiimide groups as described in German Pat. No. 1,092,007 (U.S. Pat. No. 3,152,162) and in German Offenlegungsschriften Nos. 2,504,400, 2,537,685 and 2,552,350; norbornane diisocyanates as described in U.S. Pat. No. 3,492,330; polyisocyanates containing allophanate groups as described e.g. in British Pat. No. 994,890, Belgian Pat. No. 761,626 and Netherlands Patent Application No. 7,102,524; polyisocyanates containing isocyanurate groups as described e.g. in U.S. Pat. No. 3,001,973, German Pat. Nos. 1,022,789; 1,222,067 and 1,027,394 and in German Offenlegungsschriften Nos. 1,929,034 and 2,004,048; polyisocyanates containing urethane groups as described e.g. in Belgian Pat. No. 752,261 or in U.S. Pat. Nos. 3,394,164 and 3,644,457; polyisocyanates containing acylated urea groups as described in German Pat. No. 1,230,778; polyisocyanates containing biuret groups as described e.g. in U.S. Pat. No. 3,124,605 and in British Pat. No. 889,050; polyisocyanates prepared by telomerization reactions as described e.g. in U.S. Pat. No. 3,654,106; polyisocyanates containing ester groups as described e.g. in British Pat. Nos. 965,474 and 1,072,956, in U.S. Pat. No. 3,567,763 and in German Pat. No. 1,231,688; reaction products of the above-mentioned isocyanates with acetals as described in German Pat. No. 1,072,385 and polyisocyanates containing polymeric fatty acid esters as described in U.S. Pat. No. 3,455,883. The distillation residues obtained from the commercial production of isocyanates and still containing isocyanate groups may also be used, optionally dissolved in one or more of the above-mentioned polyisocyanates. Any mixtures of the above-mentioned polyisocyanates may also be used.

The commercially readily available polyisocyanates are generally particularly preferred, e.g. 2,4- and 2,6-tolylenediisocyanate and mixtures of these isomers ("TDI"); polyphenyl-polymethylene polyisocyanates which may be prepared by aniline/formaldehyde condensation followed by phosgenation ("crude MDI"); and polyisocyanates containing carbodiimide groups, urethane groups, allophanate groups, isocyanurate groups, urea groups or biuret groups ("modified polyisocyanates"), particularly those modified polyisocyanates which are derived from 2,4- and/or 2,6-tolylene diisocyanate or from 4,4'- and/or 2,4'-diphenylmethane diisocyanate.

The starting components for production of the polyurethane products may also include compounds, generally having a molecular weight of from 400 to 10,000 which contain at least two isocyanate-reactive hydrogen atoms. In addition to compounds containing amino groups, thiol groups or carboxyl groups, the preferred compounds are those containing hydroxyl groups, especially those having a molecular weight of from 500 to 7000, preferably from 1000 to 5000 and which have from 2 to 8 hydroxyl groups. Suitable hydroxyl compounds include polyesters, polyethers, polythioethers, polyacetals, polycarbonates and polyesteramides containing at least 2, generally from 2 to 8, preferably from 2 to 4 hydroxyl groups. The polyesters having hydroxyl groups may be, for example, reaction products of polyhydric (preferably dihydric alcohols, optionally with the addition of trihydric alcohols), and polybasic, (preferably dibasic) carboxylic acids. Instead of the free polycarboxylic acids, the corresponding polycarboxylic acid anhydrides or polycarboxylic acid esters of lower alcohols or mixtures thereof may be used for the preparation of the polyesters. The polycarboxylic acids may be aliphatic, cycloaliphatic, aromatic and/or heterocyclic; they may be substituted, for example with halogen atoms, and/or they may be unsaturated.

The following are examples of such carboxylic acids and their derivatives: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimerized and trimerized unsaturated fatty acids optionally mixed with monomeric unsaturated fatty acids such as oleic acid, dimethyl terephthalate and terephthalic acid-bis-glycol esters. Suitable polyhydric alcohols include e.g. ethylene glycol, propylene glycol (1,2) and -(1,3), butylene glycol-(1,4) and -(2,3), hexanediol-(1,6), octanediol-(1,8), neopentyl glycol, 1,4-bishydroxymethylcyclohexane, 2-methyl-1,3-propanediol, glycerol, trimethylolpropane, hexanetriol-(1,2,6)-butanetriol-(1,2,4), trimethylolethane, pentaerythritol, quinitol, mannitol, sorbitol, formitol, methyl glycoside, diethylene glycol, triethylene glycol, tetraethylene glycol and higher polyethylene glycols, dipropylene glycol and higher polypropylene glycols and dibutylene glycol and higher polybutylene glycols. The polyesters may contain a proportion of carboxyl end groups. Polyesters of lactones may also be used, e.g. of ε-caprolactone, or polyesters of hydroxycarboxylic acids such as ω-hydroxycaproic acid.

The polyethers which may be used according to the present invention, which have at least 2, generally from 2 to 8, and preferably 2 or 3 hydroxyl groups, are also generally known and may be prepared by, for example, polymerization of epoxides such as ethylene oxide, propylene oxide, butylene oxide, tetrahydrofuran, styrene oxide or epichlorohydrin, either on their own, e.g. in the presence of Lewis catalysts such as $BF_3$, or by the chemical addition of these epoxides, preferably of ethylene oxide and propylene oxide, alone, as mixtures or successively, to starting components which have reactive hydrogen atoms. Suitable starting components include water, ammonia, and alcohols such as ethylene glycol, propylene glycol-(1,3) or -(1,2), trimethylolpropane, glycerol, sorbitol, 4,4'-dihydroxy-diphenylpropane, and amines such as aniline, ethanolamine or ethylene diamine. Sucrose polyethers such as those described, for example, in German Auslegeschriften Nos. 1,176,358 and 1,064,938 and polyethers started on formitol or formose (German Offenlegungsschriften Nos. 2,639,083 and 2,737,951) may also be used according to the present invention. It is in many cases preferred to use polyethers which contain predominant amounts of primary OH groups (up to 90% by weight, based on all the OH groups present in the polyether). Polybutadienes containing OH groups are also suitable for the purpose of the present invention.

Particularly to be included among the polythioethers useful are the condensation products of thiodiglycol obtained by reaction on their own and/or with other glycols, dicarboxylic acids, formaldehyde, aminocarboxylic acids or aminoalcohols. These products may be, for example, polythio mixed ethers, polythioether esters or polythioether ester amides, depending on the cocomponents.

Suitable polyacetals include, for example, the compounds which may be prepared from glycols such as diethylene glycol, triethylene glycol, 4,4'-dioxethoxydiphenyldimethylmethane, hexanediol and formaldehyde. Polyacetals suitable for the purpose of the present invention may also be prepared by the polymerization of cyclic acetals such as trioxane (German Offenlegungsschrift No. 1,694,128).

Suitable polycarbonates having hydroxyl groups include known compounds of this type such as those obtained e.g. by the reaction of diols such as propanediol-(1,3), butane-diol-(1,4) and/or hexanediol-(1,6), diethyleneglycol, triethyleneglycol, tetraethyleneglycol or thiodiglycol with diarylcarbonates such as diphenylcarbonate or phosgene (German Auslegeschriften No. 1,694,080, 1,915,908 and 2,221,751; German Offenlegungsschrift No. 2,605,024).

Among the polyester amides and polyamides are to be included, for example, the predominantly linear condensates obtained from polybasic saturated or unsaturated carboxylic acids or their anhydrides and polyvalent saturated or unsaturated amino alcohols, diamines, polyamines or mixtures thereof.

Polyhydroxyl compounds already containing urethane or urea groups and modified or unmodified natural polyols such as castor oil or carbohydrates, e.g. starch, may also be used. Addition products of alkylene oxides and phenol formaldehyde resins or of alkylene oxides and urea formaldehyde resins may also be used according to the present invention.

The polyhydroxyl compounds mentioned above may be modified in various ways before they are used in the polyisocyanate polyaddition process. According to German Offenlegungsschriften Nos. 2,210,839 (U.S. Pat. No. 3,849,515) and 2,544,195, for example, a mixture of various polyhydroxyl compounds (e.g. of a polyether polyol and a polyester polyol) may be condensed by etherification in the presence of a strong acid to form a higher molecular polyol built up of different segments which are connected by ether bridges. It is also possible, for example, to introduce amide groups into the polyhydroxyl compounds as described in German Offenlegungsschrift No. 2,559,372 or to introduce triazine groups by reaction with polyfunctional cyanic acid esters as described in German Offenlegungsschrift No. 2,620,487. The reaction of a polyol with less than the equivalent quantity of a diisocyanatocarbodiimide followed by the reaction of the carbodiimide group with an amine, amide, phosphite or carboxylic acid results in polyhydroxyl compounds which contain guanidine, phosphonoformamidine or acylurea groups (German Offenlegungsschriften Nos. 2,714,289, 2,714,292 and 2,714,293). It is particularly interesting in some cases to convert the higher molecular polyhydroxyl compound partly or completely into the corresponding anthranilic acid ester by reaction with isatoic acid anhydride, as described in German Offenlegungsschriften Nos. 2,019,432 and 2,619,840 and in U.S. Pat. Nos. 3,808,250, 3,975,428 and 4,016,143. Higher molecular weight compounds which have aromatic amino end groups are obtained in this way.

According to German Offenlegungsschrift No. 2,546,536 and U.S. Pat. No. 3,865,791, higher molecular compounds containing amino end groups are obtained by the reaction of isocyanate prepolymers with hydroxyl group-containing enamines, aldimines or ketimines followed by hydrolysis. Other methods of preparation of higher molecular compounds containing amino end groups or hydrazide end groups have been described in German Offenlegungsschrift No. 1,694,152 (U.S. Pat. No. 3,625,871).

According to the present invention, in preparing the polyurethane products, there may also be used polyhydroxyl compounds which contain high molecular weight polyadducts or polycondensates or polymers in a finely dispersed or dissolved form. Polyhydroxyl compounds of this type are obtained when, for example, polyaddition reactions (e.g. reactions between polyisocyanates and aminofunctional compounds) or polycondensation reactions (e.g. between formaldehyde and phenols and/or amines) are carried out in situ in the above-mentioned hydroxyl compounds. Processes of this kind have been described, for example, in German Auslegeschriften Nos. 1,168,075 and 1,260,142 and in German Offenlegungsschriften Nos. 2,324,134, 2,423,984, 2,512,385, 2,513,815, 2,550,796, 2,550,797, 2,550,833, 2,550,862, 2,633,293 and 2,639,254. According to U.S. Pat. No. 3,869,413 and German Offenlegungsschrift No. 2,550,860, such polyhydroxyl compounds may also be obtained by mixing a previously prepared aqueous polymer dispersion with a polyhydroxyl compound and then removing the water from the mixture.

Polyhydroxyl compounds modified with vinyl polymers are also suitable for the process according to the present invention, e.g. the compounds obtained by the polymerization of styrene and acrylonitrile in the presence of polyethers (U.S. Pat. Nos. 3,383,351, 3,304,273, 3,523,093 and 3,110,695; and German Auslegeschrift No. 1,152,536) or polycarbonate polyols (German Pat. No. 1,769,795; U.S. Pat. No. 3,637,909). Polyether polyols which have been modified according to German Offenlegungschriften Nos. 2,442,101, 2,644,922 and 2,646,141 by graft polymerization with vinyl phosphonic acid esters and optionally (meth)acrylonitrile, (meth)acrylamide or OH—functional (meth)acrylic acid esters give rise to synthetic products of exceptionally high flame resistance. Polyhydroxyl compounds into which carboxyl groups have been introduced by radical graft polymerization with unsaturated carboxylic acids and optionally other olefinically unsaturated monomers (German Offenlegungsschriften Nos. 2,714,291, 2,739,620 and 2,654,746) are particularly advantageously used in combination with mineral fillers.

When modified polyhydroxyl compounds of the type mentioned above are used as starting components for the polyisocyanate polyaddition process, the products obtained are in many cases polyurethane resins which have substantially improved mechanical properties.

Representatives of the many types of compounds which can be used according to the present invention have been described, for example, in High Polymers, Vol. XVI, "Polyurethanes, Chemistry and Technology" by Saunders-Frisch, Interscience Publishers, New York, London, Volume I, 1962, pages 32 to 42 and pages 44 to 54 and Volume II, 1964, pages 5-6 and 198-199 and in Kunststoff-Handbuch, Volume VII, Vieweg-Höchtlen, Carl-Hanser-Verlag, Munich, 1966, e.g. on pages 45 to 71. There may, of course, also be used mixtures of the above-mentioned compounds which have a molecular weight of from 400 to 10,000 and contain at least two isocyanate-reactive hydrogen atoms, e.g. mixtures of polyethers and polyesters.

It is particularly advantageous in some cases to use a combination of low melting and high melting polyhydroxyl compounds (German Offenlegungsschrift No. 2,706,297).

Compounds having a molecular weight of from 32 to 400 and having at least two isocyanate-reactive hydrogen atoms may also be used as the starting components for the production of polyurethanes according to the instant invention. These also include compounds containing hydroxyl groups and/or amino groups and/or thiol groups and/or carboxyl groups, and preferably hydroxyl groups and/or amino groups. These materials serve as chain lengthening agents or cross-linking agents. These compounds generally have from 2 to 8, and preferably from 2 to 4 isocyanate-reactive hydrogen atoms. These compounds having a molecular weight of from 32 to 400 and containing at least two isocyanate-reactive hydrogen atoms may also be used as a mixture of such compounds.

The following are mentioned as examples of such compounds: ethylene glycol; propylene glycol-(1,2) and -(1,3); butylene glycol-(1,4) and -(2,3); pentanediol-(1,5); hexanediol-(1,6); octanediol-(1,8); neopentylglycol; 1,4-bis-hydroxymethyl-cyclohexane; 2-methyl-1,3-propanediol; dibromobutenediol (U.S. Pat. No. 3,723,392); glycerol; trimethylolpropane; hexanetriol-(1,2,6); trimethylolethane; pentaerythritol; quinitol; mannitol; sorbitol, castor oil; diethylene glycol; triethylene glycol, tetraethyleneglycol; higher polyethylene glycols having a molecular weight of up to 400; dipropylene glycol; higher polypropylene glycols having a molecular weight of up to 400; dibutylene glycol; higher polybutylene glycols having a molecular weight of up to 400; 4,4'-dihydroxydiphenylpropane; dihydroxymethylhydroquinone; ethanolamine; diethanolamine; N-methyldiethanolamine; triethanolamine and 3-aminopropanol.

Solutions of polyisocyanate polyaddition products, in particular of polyhydrazodicarbonamides and/or polyurethane ureas containing ionic groups, in low molecular, polyhydric alcohols may also be used as polyol components according to the present invention (German Offenlegungsschrift No. 2,638,759).

The following are examples of diamines which are suitable according to the present invention: ethylene diamine, 1,4-tetramethylenediamine, 1,11-undecamethylenediamine, 1,12-dodecamethylenediamine and mixtures thereof, 1-amino-3,3,5-trimethyl-5-aminomethylcyclohexane ("isophorone diamine"), 2,4- and 2,6-hexahydro-tolylenediamine and mixtures thereof, perhydro-2,4'- and -4,4'-diaminodiphenylmethane, p-xylylenediamine, bis-(3-aminopropyl)-methylamine, diamino-perhydroanthracenes (German Offenlegungsschrift No. 2,638,731) and cycloaliphatic triamines as described in German Offenlegungsschrift No. 2,614,244. Hydrazine and substituted hydrazines, e.g. methylhydrazine, N,N'-dimethylhydrazine and their homologues and acid dihydrazides may also be used according to the present invention, e.g. carbodihydrazide, oxalic acid dehydrazide, the dihydrazides of malonic succinic, glutaric, adipic, β-methyladipic, sebacic, hydracrylic and terephthalic acid; semicarbazido-alkylene hydrazides, e.g. β-semicarbazidopropionic acid hydrazide (German Offenlegungsschrift No. 1,770,591), semicarbazidoalkylene carbazic esters, e.g. 2-semicarbazidoethyl-carbazic esters (German Offenlegungsschrift No. 1,918,504) or other aminosemicarbazido compounds such as β-aminoethyl-semicarbazidocarbonate (German Offenlegungsschrift No. 1,902,931). The amino groups may be partly or completely blocked by aldimine or ketimine groups to control their activity (U.S. Pat. No. 3,734,894; German Offenlegungsschrift No. 2,637,115).

The following are given as examples of suitable aromatic diamines: bis-anthranilic acid esters as described in German Offenlegungsschriften Nos. 2,040,644 and 2,160,590; 3,5- and 2,4-diaminobenzoic acid esters as described in German Offenlegungsschrift No. 2,025,900; the diamines having ester groups as described in German Offenlegungsschriften No. 1,803,635 (U.S. Pat. Nos. 3,681,290 and 3,736,350), 2,040,650 and 2,160,589; diamines having ether groups as described in German Offenlegungsschriften Nos. 1,770,525 and 1,809,172 (U.S. Pat. Nos. 3,654,364 and 3,736,295); 2-halogen-1,3-phenylenediamines optionally substituted in the 5-position (German Offenlegungsschriften Nos. 2,001,772; 2,025,896 and 2,065,869); 3,3'-dichloro-4,4'-diamino-diphenylmethane; tolylene diamine, 4,4'-diamino-diphenylmethane; 4,4'-diaminodiphenyldisulphides (German Offenlegungsschrift No. 2,404,976); diaminodiphenyldithioethers (German Offenlegungsschrift No. 2,509,404); aromatic diamines substituted by alkylthio groups (German Offenlegungsschrift No. 2,638,760); diamino-benzene phosphonic acid esters (German Offenlegungsschrift No. 2,459,491); aromatic diamines containing sulphonate or carboxylate groups (German Offenlegungsschrift No. 2,720,166) and high melting diamines as described in German Offenlegungsschrift No. 2,635,400. Examples of aliphatic-aromatic diamines include the aminoalkylthioanilines as described in German Offenlegungsschrift No. 2,734,574.

As chain lengthening agents there may also be used according to the present invention compounds such as 1-mercapto-3-aminopropane, substituted or unsubstituted amino acids such as glycine, alanine, valine, serine and lysine and substituted or unsubstituted dicarboxylic acids, for example, succinic acid, adipic acid, phthalic acid, 4-hydroxyphthalic acid and 4-aminophthalic acid.

Compounds which are monofunctional in their reaction with isocyanates, i.e. so-called chain breakers, may also be used in proportions of from 0.01 to 10% by weight, based on the polyurethane solid content. Examples of such monofunctional compounds include monoamines such as butylamine and dibutylamine, octylamine, stearylamine, N-methyl-stearylamine, pyrrolidine, piperidine and cyclohexylamine, monohydric alcohols such as butanol, 2-ethylhexanol, octanol and dodecanol and various amyl alcohols, cyclohexanol and ethylene glycol monoethylether.

Auxiliary agents and additives may also optionally be used in the production of the polyurethane products herein. Water and/or readily volatile inorganic or organic substances may be used as blowing agents. Organic blowing agents include e.g. acetone, ethylacetate, halogen substituted alkanes such as methylene chloride, chloroform, ethylidene chloride, vinylidene chloride, monofluorotrichloromethane, chlorodifluoromethane, dichlorodifluoromethane, butane, hexane, heptane and diethylether; as inorganic blowing agents there may be used e.g. air, $CO_2$ or $N_2O$. The effect of a blowing agent may also be obtained by the addition of compounds which decompose at temperatures above room temperature to liberate gases such as nitrogen, e.g. azo compounds such as azo dicarbonamide or azoisobutyric acid nitrile. Other examples of blowing agents and details concerning the use of blowing agents may be found in Kunststoff-Handbuch Volume VII published by Vieweg and Höchtlen, Carl-Hanser Verlag, Munich 1966, e.g. on pages 108 and 109, 453 to 455 and 507 to 510. Catalysts for the polyurethane reaction may also be used. These include tertiary amines such as triethylamine, tributylamine, N-methyl-morpholine, N-ethyl-morpholine, N,N,N',N'-tetramethyl-ethylenediamine, pentamethyl-diethylenetriamine and higher homologues (German Offenlegungsschriften Nos. 2,624,527 and 2,624,528), 1,4-diazabicyclo-(2,2,2)-octane, N-methyl-N'-dimethylaminoethylpiperazine, bis-(dimethylaminoalkyl)-piperazine (German Offenlegungsschrift No. 2,636,787), N,N-dimethylbenzylamine, N,N-dimethylcyclohexylamine, N,N,N-diethylbenzylamine, bis-(N,N-diethylaminoethyl)-adipate, N,N',N'-tetramethyl-1,3-butanediamine, N,N-dimethyl-β-phenylethylamine, 1,2-dimethylimidazole, 2-methylimidazole, monocyclic and bicyclic amidines (German Offenlegungsschrift No. 1,720,633), bis-(dialkylamino)-alkylethers (U.S. Pat. No. 3,330,782, German Auslegeschrift No. 1,030,558 and German Offenlegungsschriften Nos. 1,804,361 and 2,618,280), and tertiary amines containing amide groups (preferably formamide groups) as described in German Offenlegungsschriften Nos. 2,523,633 and 2,723,292. The known Mannich bases of secondary amines such as dimethylamine and aldehydes, preferably formaldehyde, or ketones such as acetone, methyl ethyl ketone or cyclohexanone and phenols such as phenol, nonylphenol or bisphenol may also be used as catalysts.

The following are examples of tertiary amines having isocyanate-reactive hydrogen atoms which may be used as catalysts: triethanolamine, triisopropanolamine, N-methyl-diethanolamine, N-ethyl-diethanolamine, N,N-dimethyl-ethanolamine, their reaction products with alkylene oxides such as propylene oxide and/or ethylene oxide, and secondary-tertiary amines as described in German Offenlegungsschrift No. 2,732,292.

Silaamines having carbon-silicon bonds may also be used as catalysts, e.g. the compounds described in German Pat. No. 1,229,290 (corresponding to U.S. Pat. No. 3,620,984), e.g. 2,2,4-trimethyl-2-silamorpholine and 1,3-diethylaminomethyl-tetramethyl-disiloxane.

Nitrogen-containing bases such as tetraalkylammonium hydroxides, alkali metal hydroxides such as sodium hydroxide, alkali metal phenolates such as sodium phenolate and alkali metal alcoholates such as sodium methylate may also be used as catalysts. Hexahydrotriazines may also be used as catalysts (German Offenlegungsschrift No. 1,769,043).

The reaction between isocyanate groups and Zerewitinoff-active hydrogen atoms can also be accelerated by lactams and azalactams. In such cases, an association is first formed between the lactam and the compound which has acidic hydrogen. Such associations and their catalytic action have been described in German Offenlegungsschriften Nos. 2,062,288, 2,062,289, 2,117,576 (U.S. Pat. No. 3,758,444), 2,129,198, 2,330,175 and 2,330,211.

Organic metal compounds may also be used as catalysts according to the present invention. In particular organo-tin compounds are useful. Apart from the compounds containing sulphur, such as di-n-octyl-tin-mercaptide. (German Auslegeschrift No. 1,769,367; U.S. Pat. No. 3,645,927), the organo-tin compounds used are preferably tin(II) salts of carboxylic acids, such as tin-(II) acetate, tin(II) octoate, tin(II) ethyl hexoate and tin(II) laurate, and the tin(IV) compounds, e.g. dibutyl tin oxide, dibutyl tin dichloride, dibutyl tin diacetate, dibutyl tin dilaurate, dibutyl tin maleate or dioctyl tin diacetate.

All the above-mentioned catalysts may, of course, be used as mixtures. Particularly interesting are the combinations of organic metal compounds and amidines, aminopyridines or hydroazinopyridines (German Offenlegungsschriften Nos. 2,434,185, 2,601,082 and 2,603,834).

Other representatives of catalysts which may be used according to the present invention and details concerning the activity of the catalysts have been described in Kunststoff-Handbuch, Volume VII, published by Vieweg and Höchtlen, Carl-Hanser-Verlag, Munich, 1966, e.g. on pages 96 to 102.

The catalysts are generally used in a quantity of between about 0.001 and 10% by weight, based on the total quantity of compounds which have at least two isocyanate-reactive hydrogen atoms.

Surface-active additives such as emulsifiers and foam stabilizers, may also be used. As emulsifiers there may be used, for example, the sodium salts of ricinoleic sulphonates or salts of fatty acids with amines, such as oleic acid diethylamine or stearic acid diethanolamine. Alkali metal or ammonium salts of sulphonic acids such as dodecylbenzene sulphonic acid or dinaphthylmethane disulphonic acid or of fatty acids such as ricinoleic acid or of polymeric fatty acids may also be used as surface-active additives.

The most important foam stabilizers used are the polyether siloxanes, especially those which are water-soluble. Structurally, these compounds generally consist of a copolymer of ethylene oxide and propylene oxide to which a polydimethylsiloxane group is attached. Foam stabilizers of this type have been described, for example, in U.S. Pat. Nos. 2,834,748, 2,917,484 and 3,629,308. Particularly interesting in many cases are the polysiloxanepolyoxyalkylene copolymers which are branched via allophanate groups as described in German Offenlegungsschrift No. 2,558,523.

Other additives which may optionally be used include reaction retarders, e.g. compounds which are acid in reaction such as hydrochloric acid or organic acid halides; cell regulators such as paraffins or fatty alcohols or dimethylpolysiloxanes; pigments, dyes and flame retarding agents, e.g. trischloroethylphosphate, tricresylphosphate or ammonium phosphate and polyphosphate; stabilizers against ageing and weathering, plasticizers, fungistatic and bacteriostatic substances and fillers such as barium sulphate, kieselguhr, carbon black or whiting.

Other examples of additives optionally used according to the present invention, such as surface-active additives, foam stabilizers, cell regulators, reaction retarders, stabilizers, flame retarding substances, plasticizers, dyes, fillers and fungistatic and bacteriostatic substances and details about the use and action of these additives may be found in Kunststoff-Handbuck, Volume VII, published by Vieweg and Höchtlen, Carl-Hanser-Verlag, Munich 1966, e.g. on pages 103 to 113.

According to the present invention, the reactants for production of the polyurethanes are brought together by the known one-shot process, prepolymer process or semi-prepolymer process, frequently using mechanical devices such as those described in U.S. Pat. No. 2,764,565. Details concerning apparatus which may also be used according to the invention are given in Kunststoff-Handbuch, Volume VII, published by Vieweg and Höchtlen, Carl-Hanser-Verlag, Munich, 1966, e.g. on pages 121 to 205.

According to the present invention, foaming may also be carried out in closed molds. In that case, the reaction mixture is introduced into a mold which may be made of a metal such as aluminum or a synthetic material, e.g. an epoxide resin. The reaction mixture foams up inside the mold to form the shaped product. Foaming inside the mold may be carried out to produce an article having a cellular structure on its surface or it may be carried out in such a way that the product has a compact skin and a cellular core. According to the invention, the desired result may be achieved by, on the one hand, introducing just sufficient foamable reaction mixture into the mold to fill the mold with foam or, on the other hand, introducing a larger quantity of reaction mixture than is necessary to fill the interior of the mold with foam. The latter method is known as "over-charging" and has been disclosed, for example, in U.S. Pat. Nos. 3,178,490 and 3,182,104.

The process of foaming inside molds is in many cases carried out with the aid of so-called "external" mold release agents such as silicone oils but so-called "internal" mold release agents may also be used, optionally as mixtures with external mold release agents as disclosed, for example, in German Offenlegungsschriften Nos. 2,121,670 and 2,307,589.

Cold setting foams may also be produced according to the present invention (see British Pat. No. 1,162,517 and German Offenlegungsschrift No. 2,153,086).

Foams may, of course, also be produced by the process of block foaming or by the known laminator process.

The reaction of the polyhydroxyl compounds which are obtainable according to the present invention (without the use of any other isocyanate-reactive components) with highly elasticizing polyisocyanates, e.g. polyisocyanates having a biuret structure (German Auslegeschrift No. 1,543,178) results in hard, light-fast, scratch-resistant and solvent-resistant coatings and lacquers. Polyether alcohols having a high functionality can be obtained by base or acid catalyzed propoxylation and/or ethoxylation of the polyols of the present invention. Among these polyether alcohols, those having high OH numbers may be used for the manufacture of rigid or semi-rigid cellular polyurethanes while those having low OH numbers may be used as starting materials for highly elastic polyurethane foams. Further details on the preparation of polyethers may be found in German Offenlegungsschrift No. 2,639,083.

Highly branched polyesters which may be used as additives to alkyd resins to improve their hardness may be obtained by reacting the mixtures of polyhydric alcohols prepared according to the present invention with polybasic carboxylic acids of the type mentioned above such as phthalic acid, isophthalic acid, terephthalic acid, tetra-and hexa-hydrophthalic acid, adipic acid or maleic acid by the usual methods of polyester condensation, for example as described in Houben-Weyl, Methoden der organischen Chemie, Vol. XIV, 12, page 40. The hydroxyl group-containing polyesters synthesized from the hydroxyl compounds which are prepared according to the invention are, of course, also suitable starting components for the production of polyurethanes.

The polyhydric alcohols prepared according to the present invention may easily be converted into hydroxyl group-containing esters by reaction with long chain aliphatic mono-carboxylic acids such as caprylic, capric, lauric, myristic, palmitic, stearic, oleic, linoleic, arachidonic or behenic acid or their derivatives, e.g. their methyl or ethyl esters or their anhydrides or mixed anhydrides. These hydroxyl esters, like the ethoxylation products of the polyols or the carbamic acid esters obtained by reacting the polyhydroxyl compounds prepared according to the invention with long chain monoisocyanates such as n-octyl, n-decyl, n-dodecyl, myristyl, cetyl or stearyl isocyanate (see e.g. K. Lindner, Tenside Volume III, Wissenschaftliche Verlagsgesellschaft Stuttgart, 1964, page 2336), represent non-ionogenic surface-active compounds which are valuable emulsifiers, wetting agents or plasticizers. The compounds according to the invention may also be used as moisturizers in cosmetics and synthetic materials but they are also suitable for use e.g. as antifreezes or as additives used in formulations for plant protection.

The following Examples serve to explain the process according to the invention. Quantities given are to be understood as parts by weight or percentages by weight unless otherwise indicated.

EXAMPLES

EXAMPLE 1 (Comparison example)

This example demonstrates that in the processes known in the art, using substantially longer times and larger quantities of catalyst, the products obtained have a higher proportion of $C_6$–$C_8$ components than the products obtained by the process according to the present invention.

250 ml of a formose solution prepared according to Example 1 of German Offenlegungsschrift No. 2,721,186 introduced into a 0.7 liter autoclave with 80 grams of Raney nickel are hydrogenated at a hydrogen pressure of 150 bar for 4 hours at 30° C., then for one hour at 60° C. and finally for one hour at 100° C.

A slightly yellowish solution of polyhydroxyl compounds containing 0.018% of reducing groups and having the following molecular distribution is obtained:
Compounds having 2 carbon atoms: 0.8
Compounds having 3 carbon atoms: 2.2
Compounds having 4 carbon atoms: 5.6
Compounds having 5 carbon atoms: 30.4
Compounds having 6 carbon atoms: 40.0
Compounds having 7 carbon atoms or more: 21.0

EXAMPLE 2 (Comparison example)

100 g of catalyst (Raney nickel/Fe in proportions of 85:15) suspended in 1 liter of water are introduced into a 3 liter refined steel autoclave and heated to the hydrogenation temperature (150° C.). The space above is then filled with hydrogen gas to an operating pressure of 150 bar. 500 ml of a 50% formose solution prepared according to Example 1 of German Offenlegungsschrift No.

2,721,186 and containing 11.1% of reducible groups (determined as carbonyl groups) are adjusted to a pH value of 10.0 with NaOH and pumped into the autoclave in the course of 6 minutes. Hydrogenation is then continued for a further 6 minutes. 500 ml of the hydrogenated solution are discharged through an upright pipe containing a frit which retains the catalyst, and the next charge is pumped in and hydrogenated in the same way as the first batch. The same procedure is adopted with 160 subsequent batches of 500 ml each. No catalyst loss is recorded after this number of cycles.

The hydrogenated solutions are collected, freed from salt over an ion exchange resin and freed from the bulk of the water in a thin layer evaporator. A yellow formitol having the following properties is obtained:

Residual water content: 1.1%
Residual carboxyl content: 0.016%
OH number: 1390
Distribution of components:
  Compounds having 2 carbon atoms: 7.9%
  Compounds having 3 carbon atoms: 22.0%
  Compounds having 4 carbon atoms: 19.0%
  Compounds having 5 carbon atoms: 19.1%
  Compounds having 6 carbon atoms: 21.0%
  Compounds having 7 or more carbon atoms: 11.0%.

EXAMPLE 3

100 g of catalyst (Raney nickel/Fe in proportions of 85/15) suspended in 1 liter of water are introduced into a 3 liter refined steel autoclave and heated to the hydrogenation temperature of 150° C. The space above the catalyst is then filled with hydrogen gas to an operating pressure of 150 bar. 500 ml of the unconcentrated 50% formitol solution obtained in Example 2 are passed over a commercial cation exchange resin which is in the H form (sulphonated polystyrene cross-linked with divinylbenzene), as a result of which the pH value settles at 3.2. The solution is left to stand for 30 minutes at 30° C. The pH of the solution is then readjusted to a value of 10.0 by passage over a commercial anion exchange resin in the OH form and the addition of sodium hydroxide. The solution which is now alkaline is pumped into the autoclave within 8 minutes and rehydrogenated for 10 minutes. 500 ml of the solution is then discharged through an upright pipe having a frit which retains the catalyst. The same procedure is adopted for 140 subsequent batches. No loss of catalyst can be observed.

The hydrogenated solutions are collected, freed from salt over an ion exchange resin and freed from water in a thin layer evaporator. A glass-clear, colorless formitol having the following composition is obtained:

Compounds having 2 carbon atoms: 7.5%
Compounds having 3 carbon atoms: 22.3%
Compounds having 4 carbon atoms: 21.8%
Compounds having 5 carbon atoms: 17.2%
Compounds having 6 carbon atoms: 20.1%
Compounds having 7 or more carbon atoms: 11.1%.

EXAMPLE 4

Preparation of a polyurethane foam

25—Parts of a polypropylene oxide (OH number 470) started on ethylene diamine.
22—parts of the formitol from Example 3,
10—parts of trichloroethylphosphate,
15—parts of monofluorotrichloromethane,
0.5—parts of dimethylbenzylamine,
0.5—parts of a commercial silicone stabilizer (L-5340 of UCC)
and
75—parts of a commercial phosgenation product of aniline/formaldehyde condensates (isocyanate content: 29%)
are vigorously mixed and the mixture is left to foam up in an open mold.

A rigid, finely cellular foam which has excellent tear resistance and dimensional stability is obtained.

What is claimed is:

1. A process for the preparation of low molecular weight polyhydric alcohols by the hydrogenation of formose solutions in the presence of metal catalysts, comprising:
   (A) introducing a formose solution at a concentration of at least 20%, the pH of which solution has been adjusted to a value of from 7.5 to 12.5, batchwise into a first reactor at a rate such that the concentration of reducible groups (determined as carbonyl groups) inside the reactor does not exceed 2% by weight;
   (B) hydrogenating said solution batchwise in the presence of a catalyst, said catalyst content remaining constant in said reactor;
   (C) withdrawing the reaction product batchwise from the first reactor when the concentration of reducible groups (determined as carbonyl groups) has fallen below 1.5% by weight;
   (D) adjusting the pH of the prehydrogenated product thus obtained to a value of from 1 to 6 and maintaining a temperature of 10° to 100° C. for from 10 minutes to 2 hours;
   (E) introducing the reaction product thus obtained batchwise into a second reactor, the pH of said product being readjusted to a value of from 7.5 to 12.5, immediately before introduction of the product into the second reactor;
   (F) hydrogenating the product batchwise in the presence of a catalyst, said catalyst content remaining constant in said reactor; and
   (G) withdrawing the reaction product batchwise from the second reactor after a dwell time of from 5 minutes to 4 hours, further characterized in that the amount of said formose solution introduced into each reactor is from 3 to 30 times the amount of catalyst present in each reactor.

2. The process of claim 1, characterized in that the individual batches are pumped in at a rate corresponding to the filling of 1/6 of the volume of each reactor in from 3 to 120 minutes.

3. The process of claim 2, characterized in that the rate of filling amounts to 1/6 of the volume of each reactor in from 5 to 30 minutes.

4. The process of claim 1, characterized in that after each batch of the first reactor has been pumped in, hydrogenation is carried out for a period amounting to from ½ to 4 times the time taken to pump in the batch.

5. The process of claim 4, characterized in that after each batch for the second reactor has been pumped in, hydrogenation is carried out for a period corresponding to from ½ to 5 times the time required for pumping in the batch.

6. The process of claim 1, characterized in that in addition to formose, the starting material to be hydrogenated contains up to 80% by weight (based on the total quantity of material to be hydrogenated) of other natural and/or synthetic sugars.

7. The process of claim 1, characterized in that catalysts containing nickel are used in both reactors of the hydrogenation.

8. The process of claim 7, characterized in that the catalyst used is Raney nickel optionally modified with iron and/or zinc.

* * * * *